United States Patent [19]

Tice

[11] Patent Number: 5,733,849
[45] Date of Patent: Mar. 31, 1998

[54] HALOPYRIDYL TRIAZOLINONE HERBICIDES AND HERBICIDAL USE THEREOF

[75] Inventor: Colin Michael Tice, Elkins Park, Pa.

[73] Assignee: Rohm and Haas Company, Phila., Pa.

[21] Appl. No.: 814,515

[22] Filed: Mar. 10, 1997

Related U.S. Application Data

[60] Provisional application No. 60/013,499, Mar. 15, 1996.
[51] Int. Cl.$^6$ .................. C07D 401/04; A01N 43/82
[52] U.S. Cl. ........................... 504/130; 546/272.4
[58] Field of Search .............. 546/272.4; 514/340; 504/130

[56] References Cited

U.S. PATENT DOCUMENTS

| | | | |
|---|---|---|---|
| 5,120,347 | 6/1992 | Hsu et al. | 71/92 |
| 5,292,762 | 3/1994 | Hsu | 514/363 |
| 5,334,726 | 8/1994 | Hsu et al. | 548/263.2 |
| 5,391,561 | 2/1995 | Hsu | 514/364 |

FOREIGN PATENT DOCUMENTS

0404498 A2  12/1990  European Pat. Off. .

*Primary Examiner*—Zinna Northington-Davis
*Attorney, Agent, or Firm*—Thomas D. Rogerson

[57] ABSTRACT

Disclosed are herbicidal halopyridyl triazolinones, herbicidal compositions comprising the halopyridyl triazolinones, and herbicidal use of the compounds and compositions. Such compounds and compositions are useful as both preemergence and postemergence herbicides in a variety of crops.

6 Claims, No Drawings

HALOPYRIDYL TRIAZOLINONE HERBICIDES AND HERBICIDAL USE THEREOF

This is a nonprovisional application of prior pending provisional application Ser. No. 60/013,499 filed Mar. 15, 1996.

This invention relates to new halopyridyl triazolinones, compositions thereof, and their use as selective herbicides which are effective against both monocot and dicot weed species in either preemergence or postemergence applications.

U.S. Pat. Nos. 5,120,347 and 5,334,726 disclose herbicidal phenyl triazolinones of formula I:

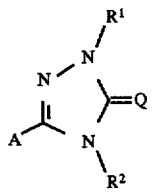

wherein A is phenyl or thienyl, Q is oxygen or sulfur, and $R^1$ and $R^2$ are a limited number of substituents. Although such compounds, as well as a wide variety of other herbicidal compounds and compositions, are known for the control of unwanted vegetation, the need continues for novel and improved herbicidal compounds and compositions, particularly in light of the variety of plant types found in both crops and weeds. This is particularly true for situations wherein a crop is infested with botanically similar weeds, for example, when a crop such as corn is infested with grassy weeds. Furthermore, weeds can become resistant to known herbicides over time. To overcome such resistance, economic and environmental considerations often favor herbicides having different modes of action, resulting from different chemical structures, than those herbicides currently used.

We have discovered a class of halopyridyl triazolinones which act as selective herbicides. This result is both unexpected and surprising in light of the fact that the closely related pyridyl triazolinthiones are known primarily for their utility as antidepressants, not herbicides (see, for example, U.S. Pat. No. 4,952,593). European Patent Application 0 404 498 A2 discloses iodoparpargyl substituted pyridyl triazolinones, exemplified by compounds such as the following compound of formula II, which are also microbicidal.

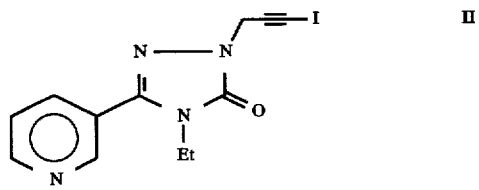

This invention provides new halopyridyl triazolinones of general formula III:

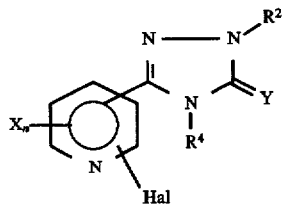

wherein
a. Hal is a halogen selected from F, Cl and Br;

b. X is selected from H, F, Cl, Br, cyano, nitro, hydroxy, mercapto, thiocyanato,($C_1$–$C_6$)alkyl, ($C_1$–$C_6$)haloalkyl, ($C_1$–$C_6$)alkoxy, halo($C_1$–$C_6$)alkoxy, ($C_2$–$C_6$)alkenylthio, ($C_2$–$C_6$)alkynylthio, ($C_1$–$C_6$)alkylthio, ($C_2$–$C_6$)alkenylsulfinyl, ($C_2$–$C_6$)alkenylsulfonyl, ($C_2$–$C_6$)alkynylsulfinyl, ($C_2$–$C_6$)alkynylsulfonyl, ($C_1$–$C_6$)alkylsulfinyl, ($C_1$–$C_6$)alkylsulfonyl, halo($C_1$–$C_6$)alkylthio, halo($C_1$–$C_6$)alkylsulfinyl, halo($C_1$–$C_6$)alkylsulfonyl, ($C_1$–$C_6$)alkylthiocarbonyl, ($C_1$–$C_6$)alkoxytrtiocarbonyl, aminothiocarbonyl, ($C_1$–$C_6$)alkylaminothiocarbonyl, di($C_1$–$C_6$)alkylaminothiocarbonyl, carboxyl, formyl, ($C_1$–$C_6$)alkylcarbonyl, ($C_1$–$C_6$)alkoxycarbonyl, ($C_1$–$C_6$)alkanoyloxy, amino, ($C_1$–$C_6$)alkylamino, di($C_1$–$C_6$)alkylamino, carbamoyl, ($C_1$–$C_6$)alkylcarbamoyl, di($C_1$–$C_6$)alkylcarbamoyl, cyano($C_1$–$C_6$)alkyl, ($C_2$–C6)alkenyl, ($C_1$–$C_6$)alkyldithionate, ($C_1$–$C_6$)alkylcarbonylthio, tri($C_1$–$C_6$)alkylsilyl, ($C_1$–$C_6$)dialkylphosphonate, ($C_1$–$C_6$)alkylphosphinate, ($C_1$–$C_6$)alkylphosphonamido, ($C_1$–$C_6$)dialkylphosphonamido, ($C_1$–$C_6$)trialkylphosphonamido, ($C_1$–$C_6$)tetraalkylphosphonamido, aminocarbonyl, ($C_1$–$C_6$)alkylaminocarbonyl, ($C_1$–$C_6$)dialkylaminocarbonyl, oximino, ($C_1$–$C_6$)alkyloximino, ($C_1$–$C_6$)dialkylhydrazone, unsubstituted or substituted phenyl, phenoxy, benzoyl, phenoxycarbonyl, phenylthio, phenyl($C_1$–$C_6$)alkyl wherein the substituents are independently selected from one to two of the group consisting of halo, cyano, nitro, hydroxy, ($C_1$–$C_6$)alkyl, ($C_1$–$C_6$)alkoxy, halo($C_1$–$C_6$)alkyl, halo($C_1$–$C_6$)alkoxy, ($C_1$–$C_6$)alkylthio, ($C_1$–$C_6$)alkylsulfinyl, ($C_1$–$C_6$)alkylsulfonyl, carboxy, formyl, ($C_1$–$C_6$)alkylcarbonyl, ($C_1$–$C_6$)alkoxycarbonyl, ($C_1$–$C_6$)alkanoyloxy, amino, ($C_1$–$C_6$)alkylamino, and di($C_1$–$C_6$)alkylamino, c. n is selected from 1 and 2;

d. $R^2$ is selected from ($C_1$–$C_8$)alkyl, ($C_3$–$C_8$)alkenyl, ($C_4$–$C_8$)alkynyl, ($C_1$–$C_4$)alkoxy($C_1$–$C_4$)alkyl; halo($C_1$–$C_8$)alkyl, halo($C_3$–$C_8$)alkenyl, halo($C_4$–$C_8$)alkynyl, halo($C_1$–$C_4$)alkoxy($C_1$–$C_4$)alkyl, ($C_1$–$C_4$)alkylthio($C_1$–$C_4$)alkyl, and halo($C_1$–$C_4$)alkylthio($C_1$–$C_4$)alkyl;

e. $R^4$ is selected from straight chain ($C_3$–$C_6$)alkynyl, ($C_1$–$C_3$)alkoxy($C_1$–$C_3$)alkyl, halo($C_3$–$C_6$)alkynyl, and halo($C_1$–$C_3$)alkoxy($C_1$–$C_3$)alkyl;

f. Y is selected from O and S; and its diastereomers, and stereoisomers; and agronomically acceptable salts thereof.

The terms "alkyl" and "alkenyl" include straight chain, branched chain, and cyclic alkyl and alkenyl groups. The term alkynyl includes straight chain and branched chain alkynyl groups. The term "alkoxy" and "alkenyloxy" includes as the alkyl portion straight chain, branched chain, and cyclic alkyl and alkenyl groups. The term "halo" preceeding any one of alkyl, alkenyl, alkynyl, or alkoxyalkyl means that at least one of the hydrogens of the group is substituted with a halogen.

Because of their high activity and selectivity, preferred compounds are those of formula I wherein: Hal is selected from F and Cl; X is selected from H, F, and Cl; n is 1; $R^2$ is selected from straight chain and branched chain ($C_2$–$C_5$) alkyl, straight chain and branched chain ($C_3$–$C_5$)alkenyl, ($C_4$–$C_5$)alkynyl, straight chain ($C_1$–$C_2$)alkoxy($C_1$–$C_2$)alkyl, straight chain and branched chain halo($C_2$–$C_8$)alkyl, straight chain and branched chain halo($C_3$–$C_5$)alkenyl, halo($C_4$–$C_5$)alkynyl, and straight chain halo($C_1$–$C_2$)alkoxy($C_1$–$C_2$)alkyl;

$R^4$ is selected from ($C_3$–$C_4$)alkynyl and ($C_1$–$C_2$)alkoxy($C_1$–$C_2$)alkyl; and Y is O.

Because of their outstanding herbicidal activity and selectivity the most preferred compounds of formula I are those wherein: Hal is selected from F and Cl; n is 1; X is selected from H, F, and Cl; $R^2$ is selected from Et, n-Pr, i-Pr, t-Bu, allyl, α-methyl-propargyl, 2,2,2-trifluoroethyl, methoxymethyl; $R^4$ is propargyl; and Y is O.

In another embodiment, this invention provides herbicidal compositions comprising one or more compounds of formula I and an agronomically acceptable carrier.

A third aspect of this invention relates to a method of controlling unwanted vegetation comprising contacting the unwanted vegetation with an herbicidally effective amount of a compound of formula I or an herbicidal composition comprising one or more compounds of formula I and an agronomically acceptable carrier.

The term "contacting" means applying one or more compounds of formula I or a composition comprising one or more compounds of formula I and an agronomically acceptable carrier to unwanted vegetation, to the locus of the unwanted vegetation, or to the growth medium of the unwanted vegetation.

Some embodiments of this invention are described in detail in the following examples.

The following general preparative method was used to synthesize the example compounds:

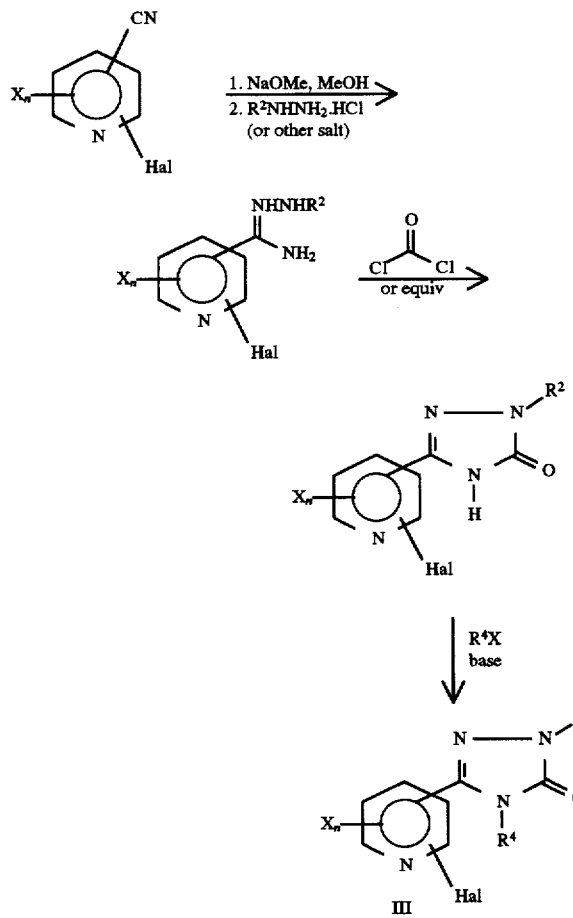

A cyanopyridine is treated with ca. 10 mol % of a sodium alkoxide in an alcohol solvent at 0°–40° C. for 2–24 hours and then 120 mol % of a hydrazine salt (e.g. a hydrochloride, hydrobromide, acetate or oxalate) is added. The mixture is stirred for 2–24 h to afford an amidrazone. The amidrazone is treated with phosgene, trichloromethyl chloroformate, ($C_1$–$C_6$)alkyl chloroformate, phenyl chloroformate or carbonyl diimidazole in the presence of an amine base such as pyridine, lutidine or triethylamine in an ether, aromatic hydrocarbon or chlorinated hydrocarbon solvent at –20° to 50° C. for 2 to 48 hours to afford a triazolinone of formula III wherein $R^4$=H. This triazolinone is treated with an alkylating agent $R^4X$, wherein X=halogen, alkanesulfonate, arenesulfonate or haloalkanesulfonate and a base e.g. an alkali metal carbonate, alkali metal hydroxide, alkali metal alkoxide or sodium hydride in an ether, ketone, alcohol, aromatic hydrocarbon or N,N-dimethylamide solvent or water or DMSO at 0° to 100° C. to afford a compound of the invention.

Compounds prepared using this general method include the following:

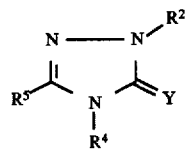

| Ex. | R2 | Y | R4 | R5 | Mp |
|---|---|---|---|---|---|
| 1 | t-Bu | O | CH2CCH | 2,6-diCl-4-pyridyl | 107–109 |
| 2 | t-Bu | O | CH2CCH | 2-Cl-4-pyridyl | Oil |
| 3 | Et | O | CH2CCH | 2-Cl-4-pyridyl | Oil |
| 4 | Et | O | CH2CCH | 2,6-diCl-4-pyridyl | 96–98 |

Table of 1H-NMR Data for Compounds which are Oils

| Ex. | Data (solvent = CDCl₃) |
|---|---|
| 2 | d 1.6 (9H,s), 2.45 (1H,t), 4.6 (2H,d), 7.65 (1H,d), 7.8 (1H,s), 8.5 (1H,d). |
| 3 | d 1.4 (3H,t), 2.45 (1H,t), 3.95 (2H,q), 4.6 (2H,d), 7.65 (1H,d), 7.8 (1H,s), 8.55 (1H,d) |

Examples of compounds which can be made using the general synthetic method include the following:

| R2 | Y | R4 | R5 |
|---|---|---|---|
| n-Pr | O | CH2CCH | 2,6-diCl-4-pyridyl |
| i-Pr | O | CH2CCH | 2-Cl-4-pyridyl |
| CH2CF3 | O | CH2CCH | 2-Cl-4-pyridyl |
| CH2CCH | O | CH2CCH | 2,6-diCl-4-pyridyl |
| CH2CH=CH2 | O | CH2CCH | 2,6-diCl-4-pyridyl |
| CH(Me)CCH | O | CH2CCH | 2-Cl-4-pyridyl |
| t-Bu | O | CH2CCH | 2-F-4-pyridyl |
| t-Bu | O | CH2CCH | 5-Cl-3-pyridyl |
| n-Pr | O | CH2CCH | 4,6-diCl-2-pyridyl |
| t-Bu | O | CH2CCMe | 2-Cl-4-pyridyl |
| t-Bu | O | CH2CCH | 2-Cl-6-Me-4-pyridyl |

SPECIFIC EXAMPLE

Preparation of 2-(t-butyl)-5-(2,6-dichloro-4-pyridyl)-4-propargyl-1,2,4-triazolin-3-one (Compound 1)

Step 1 —Preparation of the Amidrazone

To a stirred suspension of 4.02 g (23.2 mmol) of 4-cyano-2,6-dichloropyridine in 30 mL of methanol at room temperature was added 0.56 g (2.6 mmol) of a 25% by weight solution of sodium methoxide in methanol. The mixture was stirred for 16 hours and 3.46 g (27.8 mmol) of t-butylhydrazine hydrochloride was added. The mixture was stirred for 6 hours at room temperature and the solvent was removed by rotary evaporation. The solid residue was shaken with 100 mL of 5% aq HCl and 100 mL of ether. The suspended solid was collected by filtration and dried under vacuum overnight to afford 4.78 g of amidrazone hydrochloride. $^1$H NMR (d6-DMSO)∂1.3 (9H, br s), 7.9 (2H,s).

Step 2 —Preparation of 2-(t-butyl)-5-(2,6-dichloro-4-pyridyl)-1,2,4-triazolin-3-one A stirred suspension of 3.51 g (11.8 mmol) of amidrazone hydrochloride in 60 mL of $CH_2Cl_2$ and 15 mL of pyridine was cooled to <5° C. in an icebath and 6.7 mL of 1.93M (12.9 mmol) phosgene in toluene was added. The icebath was allowed to melt and the mixture was stirred at room temperature for 24 hours. The solvent was removed by rotary evaporation and the residue was dissolved in 150 mL of ethyl acetate, washed with two 50 mL portions of 5% aqueous HCl and 50 mL of brine and dried over $MgSO_4$. Removal of the solvent left 2.06 g of 2-(t-butyl)-5-(2,6-dichloro-4-pyridyl)-1,2,4-triazolin-3-one as a reddish solid. $^1$H NMR (d6-DMSO)∂1.7 (9H,s), 7.75 (2H,s).

Step 3 —Preparation of 2-(t-butyl)-5-(2,6-dichloro-4-pyridyl)-4-propargyl-1,2,4-triazolin-3-one To 2.06 g (7.2 mmol) of crude 2-(t-butyl)-5-(2,6-dichloro-4-pyridyl)-1,2,4-triazolin-3-one were added 30 mL of ethyl acetate, 1 drop of water, and 1.00 g (7.30 mmol) of powdered $K_2CO_3$. The mixture was heated to reflux and after 15 min 1.10 g (7.4 mmol) of an 80% by weight solution of propargyl bromide in toluene was added. Refluxing was continued for 2.5 hours. The mixture was cooled, diluted with 175 mL of ethyl acetate, washed with 25 mL of water, and dried over $MgSO_4$. Reomoval of the solvent left 2.18 g of crude product as a reddish solid. The crude product was combined with 0.69 g of material from another run and purified by flash chromatography first on a silica gel column and then on a neutral alumina column eluted portionwise in both cases with ether hexane mixtures containing successively greater percentages of ether to afford 0.97 g of 2-(t-butyl)-5-(2,6-dichloro-4-pyridyl)-4-propargyl-1,2,4-triazolin-3-one (Compound 1) as a white solid, m.p. 107°–109° C. 1H-NMR $(CDCl_3)$∂1.6 (9H,s), 2.45 (1H,t), 4.6 (2H,d), 7.75 (2H,s).

The compounds and compositions of this invention are useful as both preemergence and postemergence herbicides on both monocot and dicot weeds. In general, they require lower doses to control weeds preemergence. Preemergence herbicides are usually applied to the soil either before, during or after seeding, but before the crop emerges. Postemergence herbicides are applied after the plants have emerged and during their growth period.

Under some conditions the compounds of the invention may be incorporated into the soil or other growth medium prior to planting a crop. This incorporation may be by any convenient means, including mixing with the soil, applying the compound to the surface of the soil and then discing or dragging into the soil to the desired depth, or by employing a liquid carrier.

The compounds of the present invention can be applied to various loci such as the soil or foliage. For such purposes these compounds can be used in the technical or pure form as prepared, as solutions, or as formulations. Solutions and formulations of the compounds may contain from 0.01 to 99.9 percent by weight of the compound. More typically the solutions and formulations will contain from 1.0 to 85 percent by weight of the compound. The compounds are usually taken up in a carrier or are formulated so as to render them suitable for subsequent dissemination as herbicides. For example, these chemical agents can be formulated as solutions, wettable powders, emulsifiable concentrates, dusts, granular formulations, pellets, aerosols, or flowable emulsion concentrates. In such formulations, the compounds are extended with liquid or solid carriers and, when desired, suitable surfactants are incorporated.

It is usually desirable, particularly in the case of foliar spray formulations, to include one or more adjuvants, such as wetting agents, spreading agents, dispersing agents, stickers, adhesives, emulsifying agents and the like in accordance with agricultural practices. Such adjuvants commonly used in the art can be found in the John W. McCutcheon, Inc. publication "Detergents and Emulsifiers, Annual." Allured Publishing Company, Ridgewood, N.J., U.S.A.

The compounds can be applied as herbicidal sprays by methods commonly employed, such as conventional high-liter hydraulic sprays, low-liter sprays, air-blast spray, aerial sprays, and dusts. The dilution and rate of application will depend upon the type of equipment employed, the method of application, crop treated, and weeds to be controlled, but the effective amount is usually from 0.01 Kg. to 10 Kg. of the compound per hectare. Preferred amounts are from 0.1 Kg to 4 Kg of the compound per hectare.

As a soil treatment the compound can be incorporated in the soil or applied to the surface of the soil, usually at a rate of from 0.01 Kg. to 10 Kg. of the active ingredient per hectare. Again, preferred amounts are from 0.1 Kg to 4 Kg of the compound per hectare. As a foliar spray, the compound is usually applied to growing plants at similar rates.

The compounds of the invention can also be mixed with fertilizers or fertilizing materials before their application. In one type of solid fertilizing composition, particles of a fertilizer or fertilizing ingredients, such as ammonium sulfate, ammonium nitrate, or ammonium phosphate, can be coated with one or more of the compounds. The solid compounds and solid fertilizing material can also be admixed in mixing or blending equipment, or they can be incorporated with fertilizers in granular formulations. Any relative proportion of fertilizer can be used which is suitable for the crops and weeds to be treated. The compounds of the invention will commonly comprise from 1% to 25% of the fertilizing composition. These compositions provide fertilizing materials which promote the rapid growth of desired plants, and at the same time control the growth of undesired plants.

For some applications, one or more other herbicides may be added to the herbicides of the present invention, thereby providing additional advantages and effectiveness. When mixtures of herbicides are employed, the relative proportions which are used will depend upon the relative efficacy of compounds in the mixture with respect to the crops and weeds to be treated. Examples of other herbicides which can be combined with those of the present invention include:

Carboxylic acid derivatives 2,3,6-trichlorobenzoic acid and its salts; 2,3,5,6-tetrachlorobenzoic acid and its salts; 2-methoxy-3,5,6-trichlorobenzoic acid and its salts; 2-methoxy-3,6-dichlorobenzoic acid and its salts; 2-methyl-3,6-dichlorobenzoic acid and its salts; 2,3-dichloro-6-methylbenzoic acid and its salts; 2,4-dichlorophenoxyacetic acid and its salts and esters; 2,4,5-trichlorophenoxyacetic acid and its salts and esters; 2-methyl-4-chlorophenoxyacetic acid and its salts and esters; 2-(2,4,5-trichlorophenoxy)propionic acid and its salts and esters;

4-(2,4-dichlorophenoxy)butyric acid and its salts and esters; 4-(2-methyl-4-chlorophenoxy)butyric acid and its salts and esters; 2,3,6-trichlorophenylacetic acid and its salts; 3,6-endoxohexahydrophthalic acid and its salts; dimethyl 2,3,5,6-tetrachloroterephthalate; trichloroacetic acid and its salts; 2,2-dichloropropionic acid and its salts; 2,3-dichloroisobutyric acid and its salts; isopropylammonium 2-(4-isopropyl-4-methyl-5-oxo-2-imidazolin-2-yl) nicotinate; 2-[4,5-dihydro-4-methyl-4-(1-methylethyl)-5-oxo-1H-imidazol-2-yl]-3-quinolinecarboxylic acid; 6-(4-isopropyl-4-methyl-5-oxo-2-imidazolin-2-yl)-m-toluic acid, methyl ester and 6-(4-isopropyl-4-methyl-5-oxo-2-imidazolin-2-yl)-p-toluic acid, methyl ester; N-(phosphomethyl)glycine isopropylammonium salt; [3,5,6-trichloro-(2-pyridinyl)oxy]acetic acid; 3,7-dichloro-8-quinolinecarboxylic acid; ammonium DL-homoalanin-4-yl (methyl)phosphinate;

Carbamic acid derivatives ethyl N,N-di(n-propyl)thiolcarbamate; n-propyl N,N-di(n-propyl)thiolcarbamate; ethyl N-ethyl-N-(n-butyl) thiolcarbamate; n-propyl N-ethyl-N-(n-butyl) thiolcarbamate; 2-chloroallyl N,N-diethyldithiocarbamate; isopropyl N-phenylcarbamate; isopropyl N-(m-chlorophenyl)carbamate; 4-chloro-2-butynyl-N-(m-chlorophenyl)carbamate; methyl N-(3,4-dichlorophenyl) carbamate; dinitro-o-(sec-butyl)phenol and its salts; pentachlorophenol and its salts; S-(4-chlorobenzyl)-N,N-diethylthiolcarbamate;

Substituted ureas 2-chloro-N-[(4-methoxy-6-methyl,1,3,5-triazin-2-yl) aminocarbonyl]-benzenesulfon-amide; 3-(3,4-dichlorophenyl)-1,1-dimethylurea; 3-phenyl-1,1-dimethylurea; 3-(3,4-dichlorophenyl)-3-methoxy-1,1-dimethylurea; 3-(4-chlorophenyl)-3-methoxy-1,1-dimethylurea; 3-(3,4-dichlorophenyl)-1-n-butyl-1-methylurea; 3-(3,4-dichlorophenyl)-1-methoxy-1-methylurea; 3-(4-chlorophenyl)-1-methoxy-1-methylurea; 3-(3,4-dichlorophenyl)-1,1,3-trimethylurea; 3-(3,4-dichlorophenyl)diethylurea; N-(4-isopropylphenyl)-N,N'-dimethylurea; dichloral urea; methyl 2-[[[[(4,6-dimethyl-2-pyrimidinyl)amino]-carbonyl]amino]sulfonyl]benzoate; N-((6-methoxy-4-methyl-1,3,5-triazin-2-yl)aminocarbonyl)-2-(2-chloroethoxy)-benzenesulfonamide; 2-[[[(4-chloro-6-methoxypyrimidine-2-yl)aminocarbonyl]amino]-sulfonyl] benzoic acid, ethyl ester; methyl 2-[[[[(4-methoxy-6-methyl-1,3,5-triazin-2-yl)amino]-carbonyl]amino]-sulfonyl]benzoate; methyl 3-[[(4-methoxy-6-methyl-1,3,5-triazin-2-yl)aminocarbonyl]aminosulfonyl]-2-thiophenecarboxylate; methyl 2-[[[[[(4,6-dimethoxypyrimidin-2-yl)amino]carbonyl]amino]sulfonyl]-methyl]benzoate; methyl 2-[[[[(4-methoxy-6-methyl-1,3,5-triazin-2-yl) methylamino]carbonyl]amino]-sulfonyl]benzoate;

Substituted triazines 2-chloro-4,6-bis(ethylamino)-s-triazine; 2-chloro-4-ethylamino-6-isopropylamino-s-triazine; 2-chloro-4,6-bis(3-methoxy-n-propylamino)-s-triazine; 2-methoxy-4,6-bis(isopropylamino)-s-triazine; 2-chloro-4-ethylamino-6-(3-methoxy-n-propylamino)-s-triazine; 2-methylmercapto-4,6-bis(isopropylamino)-s-triazine; 2-methylmercapto-4,6-bis(ethylamino)-2-triazine; 2-methylmercapto-4-ethylamino-6-isopropylamino-s-triazine; 2-chloro-4,6-bis(isopropylamino)-s-triazine; 2-methoxy-4-ethylamino-6-isopropylamino-s-triazine; 2-methylmercapto-4-(2-methoxyethylamino)-6-isopropylamino-s-triazine; 4-amino-6-(t-butyl)-3-(methylthio)-1,2,4-triazine-5(4H)-one;

Diphenyl Ether Derivatives 2,4-dichloro-4'-nitrodiphenyl ether; 2,4,6-trichloro-4'-nitrodiphenyl ether; 2,4-dichloro-6-fluoro-4'-nitrodiphenyl ether; 3-methyl-4'-nitrodiphenyl ether; 3,5-dimethyl-5'-nitrodiphenyl ether; 2,4'-dinitro-4-(trifluoromethyl)diphenyl ether; 2,4-dichloro-3'-methoxy-4'-nitrodiphenyl ether; sodium 5-(2-chloro-4-(trifluoromethyl)phenoxy)-2-nitrobenzoate; 2-chloro-1-(3-ethoxy-4-nitrophenoxy)-4-(trifluoromethyl)benzene; 1-(carboethoxy)ethyl 5-[2-chloro-4-(trifluoromethyl)-phenoxyl]-2-nitrobenzoate; 5-[2-chloro-4-(trifluoromethyl)phenoxyl]-N-(methylsulphony)-2-nitrobenzamide;

Anilides 2-chloro-N-(2-ethyl-6-methylphenyl)-N-(2-methoxy-1-methylethyl)acetamide; 2-chloro-2',6'-diethyl-N-(2-propyloxyethyl)acetanilide; N-(3,4-dichlorophenyl) propionamide; N-(3,4-dichlorophenyl)methacrylamide; N-(3-chloro-4-methylphenyl)-2-methylpentanamide; N-(3,4-dichlorophenyl)trimethylacetamide; N-(3,4-dichlorophenyl)-alpha,alpha-dimethylvaleramide; N-isopropyl-N-phenylchloroacetamide; N-n-butoxymethyl-N-(2,6-diethylphenyl)chloroacetamide; N-methoxymethyl-N-(2,6-diethylphenyl)chloroacetamide;

Oxyphenoxy herbicides 2-(4-(2,4-dichlorophenoxy)phenoxy)methyl propionate; methyl 2-(4-(3-chloro-5-(trifluoromethyl)-2-pyridinyloxy) phenoxy)propanoate; butyl (R)-2-[4-[5-(trifluoromethyl)-2-pyridinyloxy]-phenoxy]propionate; ethyl 2-[4-[(6-chloro-2-benzoxazolyl)oxy]phenoxy]propanoate; butyl 2-[4-[[5-(trifluoromethyl)-2-pyridinyl]oxy]phenoxy]propionate; 2-[4-[(6-chloro-2-quinoxalinyl)oxy]phenoxy]propionic acid, ethyl ester;

Uracils 5-bromo-3-s-butyl-6-methyluracil; 5-bromo-3-cyclohexyl-1,6-dimethyluracil; 3-cyclohexyl-5,6-trimethyleneuracil; 5-bromo-3-isopropyl-6-methyluracil; 3-tert-butyl-5-chloro-6-methyluracil;

Nitriles 2,6-dichlorobenzonitrile; diphenylacetonitrile; 3,5-dibromo-4-hydroxybenzonitrile; 3,5-diiodo-4-hydroxybenzonitrile;

Other organic herbicides 2-chloro-N,N-diallylacetamide; N-(1,1-dimethyl-2-propynyl)-3,5-dichlorobenzamide; maleic hydrazide; 3-amino-1,2,4-triazole; monosodium methanearsonate; disodium methanearsonate; N,N-dimethyl-alpha,alpha-diphenylacetamide; N-N-di(n-propyl)-2,6-dinitro-4-(trifluoromethyl)aniline; N,N-di(n-propyl)-2,6-dinitro-4-methylaniline; N,N-di(n-propyl)-2,6-dinitro-4-methylsulfonylaniline; O-(2,4-dichlorophenyl)-O-methyl isopropylphosphoramidothioate; 4-amino-3,5,6-trichloropicolinic acid; 2,3-dichloro-1,4-naphthoquinone; di(methoxythiocarbonyl)disulfide; 3-(1-methylethyl)-1H-2,1,3-benzothiadiazin-(4)3H-one-2,2-dioxide; 6,7-dihydrodipyridol[1,2-a:2',1'-c]pyrazidiium salts; 1,1'-dimethyl-4,4'-bipyridinium salts; 3,4,5,6-tetrahydro-3,5-dimethyl-2-thio-2H-1,3,5-thiadiazine; 2-[1-(ethoxyimino) butyl]-5-[s-(ethylthio)propyl]-3-hydroxy-2-cyclohexen-1-one; 2-(2-chlorophenyl)methyl-4,4-dimethyl-3-isoxazolidinone; N-(1-ethylpropyl)-3,4-dimethyl-2,6-dinitrobenzamide; 4-chloro-5-(methylamino)-2-(α,α,α-trifluoro-m-toluyl-3-(2H)-pyridazinone; 2-(3,5-dichlorophenyl)-2-(2,2,2-trichloromethyl)oxirane.

The herbicidal activity and selectivity of a number of example compounds of the present invention towards a variety of common weeds was evaluated using the following test procedure:

Seeds of selected plants were planted in flats or pots. For preemergence tests, immediately after planting the test compound was sprayed directly onto the soil surface. The flats or pots were placed in the greenhouse and then watered. For postemergence tests, the seeds were allowed to germinate and grow for 10 to 21 days prior to application of the test compound. Before application of the test compound, each series of test plants was selected for uniformity, size, and stage of development. The test plants were then treated with the test compound, returned to the greenhouse and watered.

The compound to be evaluated was dissolved in an appropriate solvent, usually acetone, and sprayed over the flats or pots using a carrier volume equivalent to approximately 100 or 200 liters per hectare at the application rate in grams per hectare specified in the following Table. Approximately 2 or 3 weeks after application of the test compound, the growth stage of the plant was determined. Each plant species was evaluated on a scale of 0–100 in which 0 equals no activity and 100 equals total control.

| | | Greenhouse Testing Results | | | | | |
|---|---|---|---|---|---|---|---|
| Example | App. | g/Ha | BYG | FOX | MA | TOM | VEL |
| 1 | PRE | 1200 | 90 | 100 | 0 | 0 | 0 |
| 1 | POST | 1200 | 0 | 0 | 0 | 75 | 0 |
| 2 | PRE | 1200 | 90 | 100 | 25 | 100 | 100 |
| 2 | POST | 1200 | 25 | 25 | 25 | 75 | 25 |
| 3 | PRE | 1200 | 75 | 90 | 0 | 90 | 25 |
| 3 | POST | 1200 | 25 | 25 | 25 | 90 | 25 |
| 4 | PRE | 1200 | 75 | 100 | 25 | 75 | 0 |
| 4 | POST | 1200 | 25 | 25 | 25 | 90 | 25 |

APP. = PRE = preemergence application, POST = postemergence application
BYG = Barnyardgrass, *Echinochloa crus-galli*
FOX = Green Foxtail, *Setaria viridis*
MA = Marigold, *Tagetes minuta*
TOM = Tomato, *Lycopersicon esculentum*
VEL = Velvetleaf, *Abutilon theophrasti*

I claim:
1. A compound of the formula:

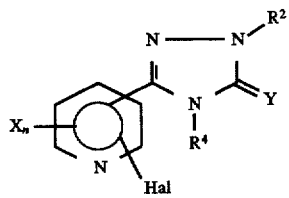

wherein
a. Hal is a halogen selected from F, Cl, and Br;
b. X is selected from H, F, Cl, Br, cyano, nitro, hydroxy, mercapto, thiocyanato, $(C_1-C_6)$alkyl, $(C_1-C_6)$haloalkyl, $(C_1-C_6)$alkoxy, halo$(C_1-C_6)$alkoxy, $(C_2-C_6)$alkenylthio, $(C_2-C_6)$alkynylthio, $(C_1-C_6)$alkylthio, $(C_2-C_6)$alkenylsulfinyl, $(C_2-C_6)$alkenylsulfonyl, $(C_2-C_6)$alkynylsulfinyl, $(C_2-C_6)$alkynylsulfonyl, $(C_1-C_6)$alkylsulfinyl, $(C_1-C_6)$alkylsulfonyl, halo$(C_1-C_6)$alkylthio, halo$(C_1-C_6)$alkylsulfinyl, halo$(C_1-C_6)$alkylsulfonyl, $(C_1-C_6)$alkylthiocarbonyl, $(C_1-C_6)$alkoxythiocarbonyl, aminothiocarbonyl, $(C_1-C_6)$alkylaminothiocarbonyl, di$(C_1-C_6)$ alkylaminothiocarbonyl, carboxyl, formyl, $(C_1-C_6)$alkylcarbonyl, $(C_1-C_6)$alkoxycarbonyl, $(C_1-C_6)$alkanoyloxy, amino, $(C_1-C_6)$ alkylamino, di$(C_1-C_6)$alkylamino, carbamoyl, $(C_1-C_6)$alkylcarbamoyl, di$(C_1-C_6)$alkylcarbamoyl, cyano$(C_1-C_6)$alkyl, $(C_2-C_6)$alkenyl, $(C_1-C_6)$alkyldithionate, $(C_1-C_6)$alkylcarbonylthio, tri$(C_1-C_6)$alkylsilyl, $(C_1-C_6)$dialkylphosphonate, $(C_1-C_6)$alkylphosphinate, $(C_1-C_6)$alkylphosphonamido, $(C_1-C_6)$ dialkylphosphonamido, $(C_1-C_6)$ trialkylphosphonamido, $(C_1-C_6)$ tetraalkylphosphonamido, aminocarbonyl, $(C_1-C_6)$ alkylaminocarbonyl, $(C_1-C_6)$dialkylaminocarbonyl, oximino, $(C_1-C_6)$alkyloximino, $(C_1-C_6)$ dialkylhydrazone, unsubstituted or substituted phenyl, phenoxy, benzoyl, phenoxycarbonyl, phenylthio, phenyl$(C_1-C_6)$alkyl wherein the substituents are independently selected from one to two of the group consisting of halo, cyano, nitro, hydroxy, $(C_1-C_6)$alkyl, $(C_1-C_6)$alkoxy, halo$(C_1-C_6)$alkyl, halo$(C_1-C_6)$alkoxy, $(C_1-C_6)$alkylthio, $(C_1-C_6)$alkylsulfinyl, $(C_1-C_6)$ alkylsulfonyl, carboxy, formyl, $(C_1-C_6)$alkylcarbonyl, $(C_1-C_6)$alkoxycarbonyl, $(C_1-C_6)$alkanoyloxy, amino, $(C_1-C_6)$alkylamino, and di$(C_1-C_6)$alkylamino;
c. n is selected from 1 and 2;
d. $R^2$ is selected from $(C_1-C_8)$alkyl, $(C_3-C_8)$alkenyl, $(C_1-C_4)$alkoxy$(C_1-C_4)$alkyl; halo$(C_1-C_8)$alkyl, halo$(C_3-C_8)$alkenyl, halo$(C_4-C_8)$alkynyl, halo$(C_1-C_4)$alkoxy$(C_1-C_4)$alkyl, $(C_1-C_4)$alkylthio$(C_1-C_4)$alkyl, and halo$(C_1-C_4)$alkylthio$(C_1-C_4)$alkyl;
e. $R^4$ is selected from straight chain $(C_3-C_6)$alkynyl, $(C_1-C_3)$alkoxy$(C_1-C_3)$alkyl, halo$(C_3-C_6)$alkynyl, and halo$(C_1-C_3)$alkoxy$(C_1-C_3)$alkyl;
f. Y is selected from O and S; and its diastereomers, and stereoisomers; or agronomically acceptable salts thereof.

2. The compound of claim 1, wherein: Hal is selected from F and Cl; X is selected from H, F, and Cl; n is 1; $R^2$ is selected from straight chain and branched chain $(C_2-C_5)$ alkyl, straight chain and branched chain $(C_3-C_5)$alkenyl, straight chain $(C_1-C_2)$alkoxy$(C_1-C_2)$alkyl, straight chain and branched chain halo$(C_2-C_5)$alkyl, straight chain and branched chain halo$(C_3-C_5)$alkenyl, halo$(C_4-C_5)$alkynyl, and straight chain halo$(C_1-C_2)$alkoxy$(C_1-C_2)$alkyl; $R^4$ is selected from $(C_3-C_4)$alkynyl and $(C_1-C_2)$alkoxy$(C_1-C_2)$ alkyl; and Y is O.

3. The compound of claim 1, wherein: Hal is selected from F and Cl; n is 1; X is selected from H, F, and Cl; $R^2$ is selected from Et, n-Pr, i-Pr, t-Bu, allyl, 2,2,2-trifluoroethyl, methoxymethyl; $R^4$ is propargyl; and Y is O.

4. An herbicidal composition comprising an herbicidally effective amount of one or more compounds of claim 1 and an agronomically acceptable carrier.

5. A method of controlling unwanted vegetation comprising contacting the unwanted vegetation with an herbicidally effective amount of a compound of claim 1.

6. A method of controlling unwanted vegetation comprising contacting the unwanted vegetation with the herbicidal composition of claim 4.

* * * * *